US011253212B2

(12) United States Patent
Jacob et al.

(10) Patent No.: US 11,253,212 B2
(45) Date of Patent: Feb. 22, 2022

(54) TILEABLE X-RAY DETECTOR CASSETTES

(71) Applicant: General Electric Company, Schenectady, NY (US)

(72) Inventors: Biju Jacob, Niskayuna, NY (US); Douglas Albagli, Clifton Park, NY (US); William Robert Ross, Kinderhook, NY (US); William Andrew Hennessy, Troy, NY (US); Eric Patrick Davis, Wynantskill, NY (US); Bruno Kristiaan Bernard De Man, Clifton Park, NY (US); Nicholas Ryan Konkle, Sussex, WI (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 23 days.

(21) Appl. No.: 16/736,607

(22) Filed: Jan. 7, 2020

(65) Prior Publication Data

US 2021/0204889 A1    Jul. 8, 2021

(51) Int. Cl.
*G01T 1/20* (2006.01)
*G01T 1/24* (2006.01)
(Continued)

(52) U.S. Cl.
CPC .............. *A61B 6/4283* (2013.01); *H04N 5/32* (2013.01); *G01T 1/20* (2013.01); *G01T 1/247* (2013.01)

(58) Field of Classification Search
CPC .......... A61B 6/4283; H04N 5/32; G01T 1/20; G01T 1/247
See application file for complete search history.

(56) References Cited

U.S. PATENT DOCUMENTS 4,467,342 A * 8/1984 Tower ................. H01L 25/0655
                                                           257/222
5,420,429 A * 5/1995 Eberhard ................ B06B 1/064
                                                           250/367
(Continued)

FOREIGN PATENT DOCUMENTS

CA        2513592 A1    2/2007

OTHER PUBLICATIONS

Thompson, A.C., et al. "A large area CMOS detector for shutterless collection of x-ray diffraction data", Journal of Physics: Conference Series, 17th Pan-American Synchrotron Radiation Instrumentation Conference (SRI2013), vol. 493, p. 1-5, 2014.

(Continued)

*Primary Examiner* — David P Porta
*Assistant Examiner* — Djura Malevic
(74) *Attorney, Agent, or Firm* — Fletcher Yoder, P.C.

(57) ABSTRACT

The present disclosure relates to the use of X-ray detector cassettes that may be abutted or overlapped to form a detector assembly suitable for imaging objects that are too large to image using a single X-ray detector cassette. Such a detector assembly may be customized in terms of the size and/or shape of the field-of-view (FOV). In certain embodiments the radiation-sensitive electronics (e.g., readout electronics) are positioned to the side of the X-ray detecting components (e.g., scintillator, TFT array, and so forth), allowing the cassette to be thin relative to other detector devices and allowing the electronics to remain outside the X-ray beam path.

20 Claims, 8 Drawing Sheets

(51) Int. Cl.
*A61B 6/00* (2006.01)
*H04N 5/32* (2006.01)

(56) References Cited

U.S. PATENT DOCUMENTS

| | | | | |
|---|---|---|---|---|
| 5,440,130 | A * | 8/1995 | Cox | H01L 27/14609 250/370.09 |
| 5,528,043 | A * | 6/1996 | Spivey | A61B 6/4233 250/208.1 |
| 5,744,806 | A * | 4/1998 | Frojd | A61B 6/14 250/370.09 |
| 5,886,353 | A * | 3/1999 | Spivey | A61B 6/502 250/370.09 |
| 5,986,279 | A * | 11/1999 | Dewaele | G01T 1/2012 250/363.01 |
| 6,175,611 | B1 * | 1/2001 | Melen | G01T 1/243 250/332 |
| 6,273,606 | B1 * | 8/2001 | Dewaele | A61B 6/5241 378/174 |
| 6,403,964 | B1 * | 6/2002 | Kyyhkynen | H04N 5/379 250/370.09 |
| 6,408,110 | B2 * | 6/2002 | Schulman | H01L 27/14601 382/312 |
| 6,614,032 | B2 * | 9/2003 | Wendlandt | G03B 42/025 206/455 |
| 6,895,077 | B2 | 5/2005 | Karellas et al. | |
| 7,009,646 | B1 * | 3/2006 | Fossum | H01L 27/14601 348/294 |
| 7,054,409 | B2 * | 5/2006 | Ross | A61B 6/032 250/370.09 |
| 7,247,858 | B2 * | 7/2007 | De Keyser | G01N 23/04 250/370.09 |
| 7,324,679 | B2 * | 1/2008 | Moriyama | G03B 42/00 382/132 |
| 7,427,749 | B2 * | 9/2008 | Spahn | H04N 5/3653 250/252.1 |
| 7,450,683 | B2 | 11/2008 | Tkaczyk et al. | |
| 7,498,583 | B2 * | 3/2009 | Shoji | A61B 6/4266 250/370.09 |
| 7,606,346 | B2 | 10/2009 | Tkaczyk et al. | |
| 7,622,719 | B2 * | 11/2009 | Spahn | G01T 1/2018 250/370.11 |
| 7,706,502 | B2 | 4/2010 | Bueno et al. | |
| 8,098,795 | B2 * | 1/2012 | Nowak | G01T 1/00 378/98.8 |
| 8,351,568 | B2 * | 1/2013 | Minnigh | A61B 6/505 378/62 |
| 8,399,847 | B2 * | 3/2013 | Konkle | G03B 42/04 250/370.09 |
| 8,586,934 | B2 * | 11/2013 | Nakatsugawa | G01T 1/2985 250/370.08 |
| 8,600,193 | B2 * | 12/2013 | Kalayeh | G06T 7/33 382/294 |
| 8,748,834 | B2 * | 6/2014 | Enomoto | H04N 5/3415 250/370.08 |
| 8,767,913 | B2 * | 7/2014 | Okuno | G01N 23/04 378/62 |
| 8,798,229 | B2 | 8/2014 | Li et al. | |
| 8,834,021 | B2 | 9/2014 | Liu et al. | |
| 9,239,392 | B2 * | 1/2016 | Gemma | G01T 1/2012 |
| 9,435,898 | B2 * | 9/2016 | Olcott | G01T 1/2018 |
| 10,058,294 | B2 * | 8/2018 | Tagawa | A61B 6/5241 |
| 10,251,614 | B2 * | 4/2019 | Wojcik | A61B 6/4411 |
| 10,342,508 | B2 * | 7/2019 | Matsushita | A61B 6/566 |
| 10,420,524 | B2 * | 9/2019 | Yamada | A61B 6/4266 |
| 10,459,094 | B2 * | 10/2019 | Simanovsky | G01T 1/2018 |
| 10,499,863 | B2 * | 12/2019 | Wojcik | A61B 6/4405 |
| 10,638,986 | B2 * | 5/2020 | Wojcik | A61B 6/4283 |
| 10,695,024 | B2 * | 6/2020 | Miyamoto | H04N 5/367 |
| 2002/0109113 | A1 * | 8/2002 | Wang | G01T 1/2014 250/584 |
| 2003/0048938 | A1 * | 3/2003 | Wang | G01T 1/2014 382/132 |
| 2003/0173493 | A1 * | 9/2003 | Homme | G01T 1/2018 250/200 |
| 2003/0200655 | A1 * | 10/2003 | Vafi | H01L 27/14658 29/854 |
| 2004/0000630 | A1 * | 1/2004 | Spartiotis | G01T 1/2964 250/208.1 |
| 2004/0071269 | A1 * | 4/2004 | Wang | G06T 3/0075 378/174 |
| 2004/0089813 | A1 * | 5/2004 | Takabayashi | G01T 1/2018 250/370.11 |
| 2004/0200971 | A1 * | 10/2004 | De Keyser | G01N 23/04 250/370.09 |
| 2005/0238138 | A1 * | 10/2005 | Imai | A61B 6/488 378/95 |
| 2006/0219926 | A1 * | 10/2006 | Shoji | H04N 5/3415 250/370.09 |
| 2007/0069111 | A1 * | 3/2007 | Spahn | H01L 27/14663 250/208.1 |
| 2008/0135765 | A1 * | 6/2008 | Vydrin | G01T 1/1642 250/359.1 |
| 2009/0097617 | A1 * | 4/2009 | Kruger | G03B 42/02 378/146 |
| 2010/0150305 | A1 * | 6/2010 | Nowak | G01T 1/00 378/22 |
| 2011/0186741 | A1 * | 8/2011 | Ohta | A61B 6/42 250/370.08 |
| 2011/0215250 | A1 * | 9/2011 | Ohta | G01T 1/24 250/370.08 |
| 2011/0233415 | A1 * | 9/2011 | Nakatsugawa | G01T 1/2985 250/370.08 |
| 2013/0004085 | A1 * | 1/2013 | Bai | G06T 3/0068 382/209 |
| 2013/0077744 | A1 * | 3/2013 | Kamiya | A61B 6/548 378/62 |
| 2013/0140467 | A1 * | 6/2013 | Kitano | H01L 27/14676 250/393 |
| 2015/0245807 | A1 * | 9/2015 | Tajima | A61B 6/5294 378/98 |
| 2015/0247936 | A1 * | 9/2015 | Gemma | G01T 1/2012 250/363.01 |
| 2016/0025865 | A1 * | 1/2016 | Wayama | A61B 6/542 250/370.07 |
| 2016/0035451 | A1 * | 2/2016 | Tsuji | A61B 6/4266 378/62 |
| 2016/0074001 | A1 * | 3/2016 | Matsushita | A61B 6/4233 378/62 |
| 2016/0249875 | A1 * | 9/2016 | Enomoto | A61B 6/5282 378/62 |
| 2016/0287202 | A1 * | 10/2016 | Miyachi | A61B 6/5241 |
| 2016/0302755 | A1 * | 10/2016 | Takagi | A61B 6/582 |
| 2017/0194374 | A1 * | 7/2017 | Jacob | H01L 27/14634 |
| 2017/0325761 | A1 * | 11/2017 | Wojcik | A61B 6/56 |
| 2018/0055465 | A1 * | 3/2018 | Nakayama | A61B 6/04 |
| 2018/0070899 | A1 * | 3/2018 | Wojcik | A61B 6/4411 |
| 2018/0182102 | A1 * | 6/2018 | Jerebko | G06T 7/0014 |
| 2018/0331137 | A1 * | 11/2018 | Jacob | H04N 5/37452 |
| 2018/0341031 | A1 * | 11/2018 | Tredwell | H04N 5/3745 |
| 2019/0216415 | A1 * | 7/2019 | Wojcik | A61B 6/4411 |
| 2020/0121270 | A1 * | 4/2020 | Wojcik | A61B 6/0407 |

OTHER PUBLICATIONS

Liu, Baodong, et al.; "An Industrial Computed Laminography Imaging System", Digital Industrial Radiology and Computed Tomography (DIR 2015), p. 1-6, Belgium, Jun. 2015.

* cited by examiner

TILEABLE X-RAY DETECTOR CASSETTES

BACKGROUND

The subject matter disclosed herein relates to X-ray inspection techniques using large field-of-view (FOV) detectors.

Non-destructive imaging techniques may be employed in various industrial, utility, and/or security contexts. In certain of the techniques a high-energy X-ray source may be employed that generates X-rays that pass through an object or manufactured item undergoing inspection. As the X-rays pass through the object, the X-rays are differentially attenuated based on the amount and/or composition of material they pass through. The X-rays, after passing through the object, may be detected on a suitable detector and the signals generated by the detector may be used to reconstruct images that reveal internal features of the imaged object without destroying or opening the object.

Such techniques may be used on objects of various sizes and shapes for which an inspection is needed. However, large industrial parts typically require high energy X-ray systems with a large field-of-view (FOV) detector to perform the inspection. In practice, it is typically infeasible to have a single detector of sufficient size to image such large industrial objects. Because such large detectors are not typically available, conventional approaches employ a small FOV detector used in a step-and-shoot mode (i.e., multiple, smaller images acquired at different positions and orientations) as opposed to a single large image acquired in one exposure. Such step-and-shoot techniques, however, are at the expense of acquisition time and may additionally require aligning and "stitching" steps if a single large image is the desired output.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, an X-ray detector cassette is provided. In accordance with this embodiment, the X-ray detector cassette comprises: a housing; one or more panel modules within the housing, and one or more electronics modules within the housing. Each panel module comprises: a scintillator and a photodiode array positioned to detect photons emitted by the scintillator. Each electronics module comprises circuitry connected to the photodiode array. The one or more electronics modules are positioned to the side of the one or more panel module so as to remain outside an X-ray beam path during operation. The X-ray detector cassette is configured to abut at least one other X-ray detector cassette such that an active area of the X-ray detector cassette abuts respective active areas of the at least one other X-ray detector cassette.

In a further embodiment, an X-ray detector assembly is provided. In accordance with this embodiment, the X-ray detector assembly comprises two or more X-ray detector cassettes and a support structure on which the two or more X-ray detector cassettes are mounted. Each X-ray detector cassette comprises: a detector panel module within a housing and an electronics module within the housing. The detector panel module comprises a scintillator and a photodiode array positioned to detect photons emitted by the scintillator. The electronics module comprises circuitry connected to the photodiode array. The electronics module is positioned to the side of the detector panel module so as to remain outside an X-ray beam path during operation. When mounted to the support structure, the two or more X-ray detector cassettes are offset from one another in a first direction corresponding to the direction of the X-ray beam path and overlap in at least a second direction such that the respective detector panel modules of the two or more X-ray detector cassettes overlap in at least the second direction.

In an additional embodiment, a method is provided for configuring an X-ray detector assembly. In accordance with this method, a field-of-view is determined for an object to be inspected. A number of detector cassettes capable of providing the field-of-view is determined. Each detector cassette comprises a detector panel module and an electronics module positioned to the side of the detector panel module so that the electronics module remains outside an X-ray beam path during imaging of the object. The number of detector cassettes is greater than one. The number of detector cassettes is mounted to a support structure to form the X-ray detector assembly providing the field-of-view. The detector cassettes, when mounted to the support structure, are offset from one another in a first direction corresponding to a direction of the X-ray beam path and overlap in at least a second direction such that the respective detector panel modules of the detector cassettes overlap in at least the second direction.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION

One or more specific embodiments will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present invention, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

As discussed herein, various implementations of the present invention may utilize flat-panel X-ray detector panels what may be provided or packaged within a housing as part of a detector. In such embodiments, such discrete detector cassette units may be combined or otherwise used together to form a multi-panel X-ray detector assembly (e.g., a tileable multi-panel X-ray detector). The multi-panel X-ray detector assembly so formed may have a large and/or custom sized or shaped field-of-view suitable for use in certain industrial imaging applications. In certain embodiments the tileable X-ray detector cassettes are designed or otherwise configured to abut (e.g., be immediately adjacent or overlap) on one or two sides (e.g., lateral sides (i.e., right and/or left sides)) or on three-sides (e.g., lateral sides plus one vertical side (i.e., a top or bottom side)) to facilitate implementation of the multi-panel X-ray detector assembly.

Figure 1:
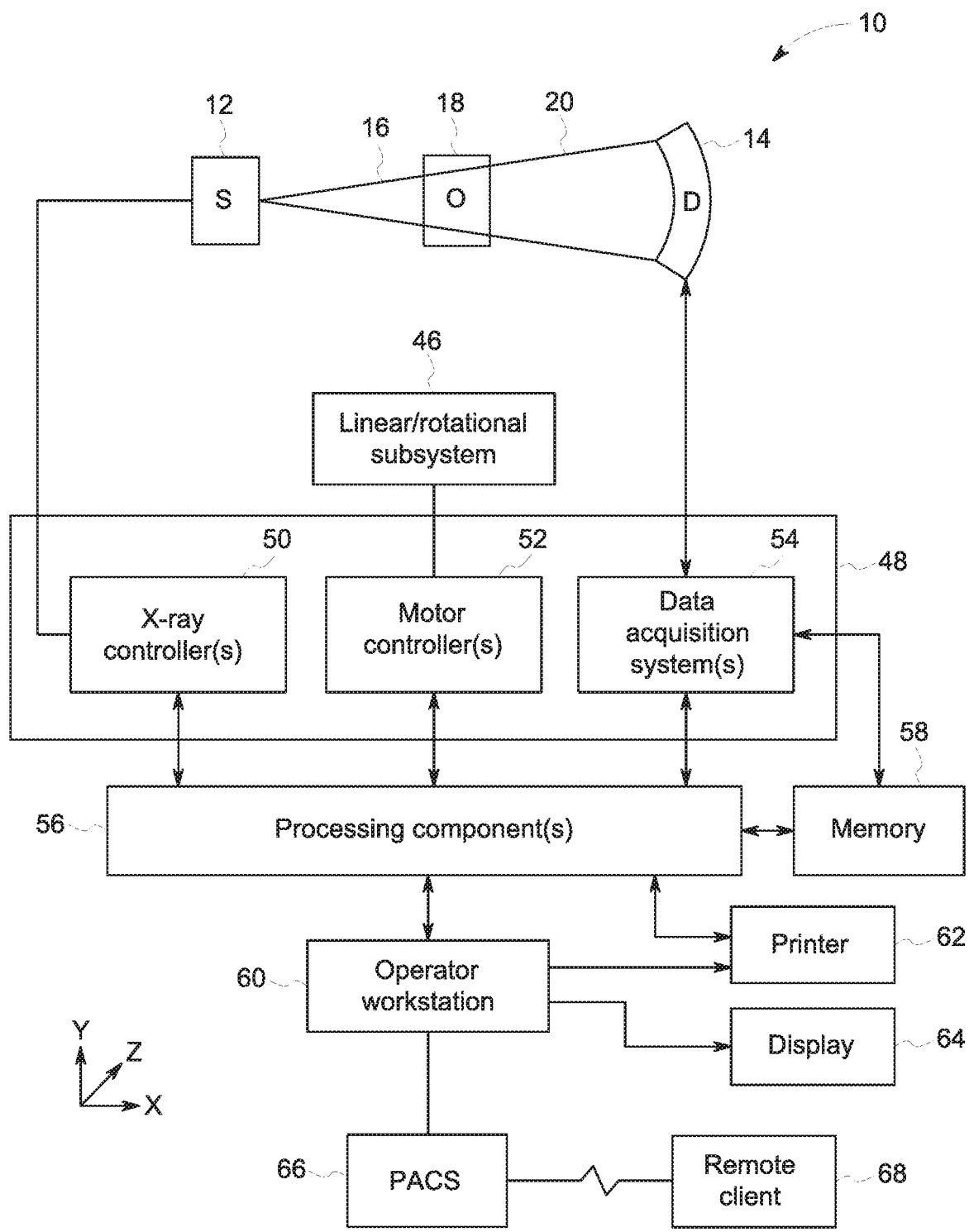
FIG. 1 is a diagrammatical view of an imaging system for use in producing images in accordance with aspects of the present disclosure.

With the preceding in mind, an example of a non-destructive testing (NDT) and/or non-destructive examination (NDE) imaging system 10 suitable for acquiring X-ray attenuation data for reconstruction as discussed herein is provided in FIG. 1. In the embodiment illustrated in FIG. 1, imaging system 10 includes a source of X-ray radiation 12 and a detector assembly 14. The X-ray source 12 may be an X-ray tube or any other source of X-ray radiation (e.g., high-energy X-ray radiation) suitable for the acquisition of NDT or NDE images. The X-rays 16 generated by the source 12 pass into a region in which an object 18 (e.g., an industrial part or manufactured good, a package or item undergoing security screening, and so forth) is positioned for examination. In the depicted example, the X-rays 16 are collimated to be a fan-shaped or cone-shaped beam, e.g., a fan-beam or cone-beam, which passes through the imaged volume. A collimator or other beam-shaping device or structure may be used to constrain the X-rays 16 to only irradiate a field-of-view (FOV) corresponding to specific portions of the object 18, such as a region-of-interest (ROI), and to avoid other portions that are not part of the examination or testing.

A portion of the X-ray radiation 20 passes through or around the object 18 and impacts a detector assembly 14. Though shown as a single structure in the schematic view of FIG. 1, in accordance with the present invention the detector assembly 14 may include multiple separate and distinct detector cassettes (which may include both detector panel components (such as a scintillator and photodiode array) and associated electronics (such as readout and/or processing electronics) packaged in a housing) that abut (i.e., be immediately adjacent or overlap) on two or more sides to form a tileable multi-panel X-ray detector assembly 14 having a large and/or custom field-of-view. The detector elements (e.g., pixels) of the detector assembly 14 produce electrical signals that represent the intensity of the incident X-rays 20. These signals are acquired and processed, as discussed herein, to reconstruct images of the features within the object 18.

The source 12 and detector assembly 14 may be moved relative to the imaged object along one or more axes during a scan procedure during which projection data is acquired. Alternatively, the object 18 may be moved or rotated (such as by placement on a turntable) relative to the source 12 and detector assembly 14 during the scan procedure. The relative movement of the object 18 with respect to the source 12 and detector assembly 14, however it is accomplished, may be initiated and/or controlled by one or more linear/rotational subsystems 46. The linear/rotational subsystems 46 may include support structures, motors, gears, bearings, and the like, that enable the rotational and/or translational movement of the object 18 and or imager components.

A system controller 48 may govern the linear/rotational subsystems 46 that initiate and/or control the relative movement of the object 18 with respect to the imager. In practice, the system controller 48 may incorporate one or more processing devices that include or communicate with tangible, non-transitory, machine readable media collectively storing instructions executable by the one or more processors to perform imaging operations. The system controller 48 may also include features that control the timing of the activation of the source 12, for example, to control the acquisition of X-ray attenuation data obtained during a particular imaging sequence. The system controller 48 may also execute various signal processing and filtration functions, such as for initial adjustment of dynamic ranges, interleaving of digital projection data, and so forth. Therefore, in general, the system controller 48 may be considered to command operation of the imaging system 10 to execute examination protocols. It should be noted that, to facilitate discussion, reference is made below to the system controller 48 as being the unit that controls acquisitions, movements, and so forth, using the imager. However, embodiments where the system controller 48 acts in conjunction with other control devices (e.g., other control circuitry local to the imagers or remote to the system 10) are also encompassed by the present disclosure.

In the present context, the system controller 48 includes signal processing circuitry and various other circuitry that enables the system controller 48 to control the operation of the source 12 and detector assembly 14 as well as the linear/rotational subsystems 46. In the illustrated embodiment, the circuitry may include an X-ray controller 50 configured to operate the X-ray source 12. Circuitry of the system controller 48 may also include one or more motor controllers 52. The motor controllers 52 may control the activation of various components that are responsible for moving the source 12 and the detector assembly 14 and/or a turntable on which the object 18 is placed.

The system controller 48 is also illustrated as including one or more data acquisition systems 54. Generally, the detector assembly 14 may be coupled to the system controller 48, and more particularly to the data acquisition systems 54. The data acquisition systems 54 may receive data collected by read out electronics of the detector assembly 14 and in certain embodiments may process the data (e.g., by converting analog to digital signals or to perform other filtering, transformation, or similar operations).

It should be noted that the tangible, non-transitory, machine-readable media and the processors that are configured to perform the instructions stored on this media that are present in the system 10 may be shared between the various components of the system controller 48 or other components of the system 10. For instance, as illustrated, the X-ray controller 50, the motor controller 52, and the data acquisition systems 54 may share one or more processing components 56 that are each specifically configured to cooperate with one or more memory devices 58 storing instructions that, when executed by the processing components 56, perform image acquisition and reconstruction techniques. Further, the processing components 56 and the memory components 58 may coordinate in order to perform various image reconstruction processes.

In one embodiment, the processing components 56 may, as part of performing reconstruction processes, stitch together data acquired on different, abutting or overlapping detector cassettes, as discussed herein, so as to reconstruct a single final image. In such implementations the processing components 56 may execute routines to extrapolate or estimate missing data where there are gaps between detector panels, may reduce or deconvolve duplicated data where detector panels overlap, or more generally merge data acquired on different detector panels for reconstruction as a single image. In one embodiment, the processing components 56 may implement or execute a neural network trained to estimate missing data or to otherwise merge data from different detector cassettes as discussed herein.

The system controller 48 and the various circuitry that it includes, as well as the processing and memory components 56, 58, may be accessed or otherwise controlled by an operator via an operator workstation 60. The operator workstation 60 may include any application-specific or general-purpose computer that may include one or more programs (for example one or more imaging programs) capable of enabling operator input for the techniques described herein. The operator workstation 60 may include various input devices such as a mouse, a keyboard, a trackball, or any other similar feature that enables the operator to interact with the computer. The operator workstation 60 may enable the operator to control various imaging parameters, for example, by adjusting certain instructions stored on the memory devices 58.

The operator workstation 60 may be communicatively coupled to a printer 62 for printing images, object data, and the like. The operator workstation 60 may also be in communication with a display 64 that enables the operator to view various parameters in real time, to view images produced by the acquired data, and the like. The operator workstation 60 may also, in certain embodiments, be communicatively coupled to a picture archiving and communication system (PACS) 66. Such a system may enable the storage of object data, object images, image acquisition parameters, and the like. This stored information may be shared throughout the imaging facility and may also be shared with other facilities, for example, a remote client 68.

As discussed with respect to FIG. 1, the detector assembly 14 may be implemented using multiple separate and distinct detector cassettes that may be configured to abut (i.e., be immediately adjacent or overlap) on one or more sides and that in combination function as the X-ray detector assembly 14. The number, size, and connection of such multiple cassettes may allow the detector assembly 14 to have a large and/or custom field-of-view relative to a single-piece detector construction. As discussed herein, the detector cassettes that together form the detector assembly 14 may be described as "buttable" or "abutting", meaning the detector cassettes may be designed or configured to abut one another on one or more sides, either with or without some degree of overlap. Depending on the embodiment, the detector panels that generate signals in response to X-ray exposure may each be in separate housings (i.e., separate detector cassettes) so as to be separable and independently movable. Alternatively, the respective detector panels may be positioned within a shared or common housing (e.g., a monolithic housing), which may help reduce the amount of space between detector panels not available for radiation detection (i.e., active area) as no space on the sides is lost due to the thickness of the housing.

Conventional detector panels typically have some or all of the readout electronics disposed behind the active area of the detector (i.e., the portion of the detector illuminated by the X-rays which generates responsive signals when illuminated by the X-rays) relative to the X-ray beam path. In such a stacked configuration, the readout electronics are effectively in the X-ray beam path of any X-rays not absorbed or stopped by the detection elements within the active area of the detector panel. In the context of high-energy X-ray imaging that is often employed in NDT or NDE, such high-energy X-rays may frequently reach the readout electronics and may damage or interfere with these electronic circuits. In contrast, in certain embodiments of the present X-ray detector as discussed below, the readout electronics may be positioned to the side of the detector panel (e.g., the scintillator and photodiode array) instead of below the detector panel, and thus out of the beam path of the high-energy X-rays during operation.

Figure 2:
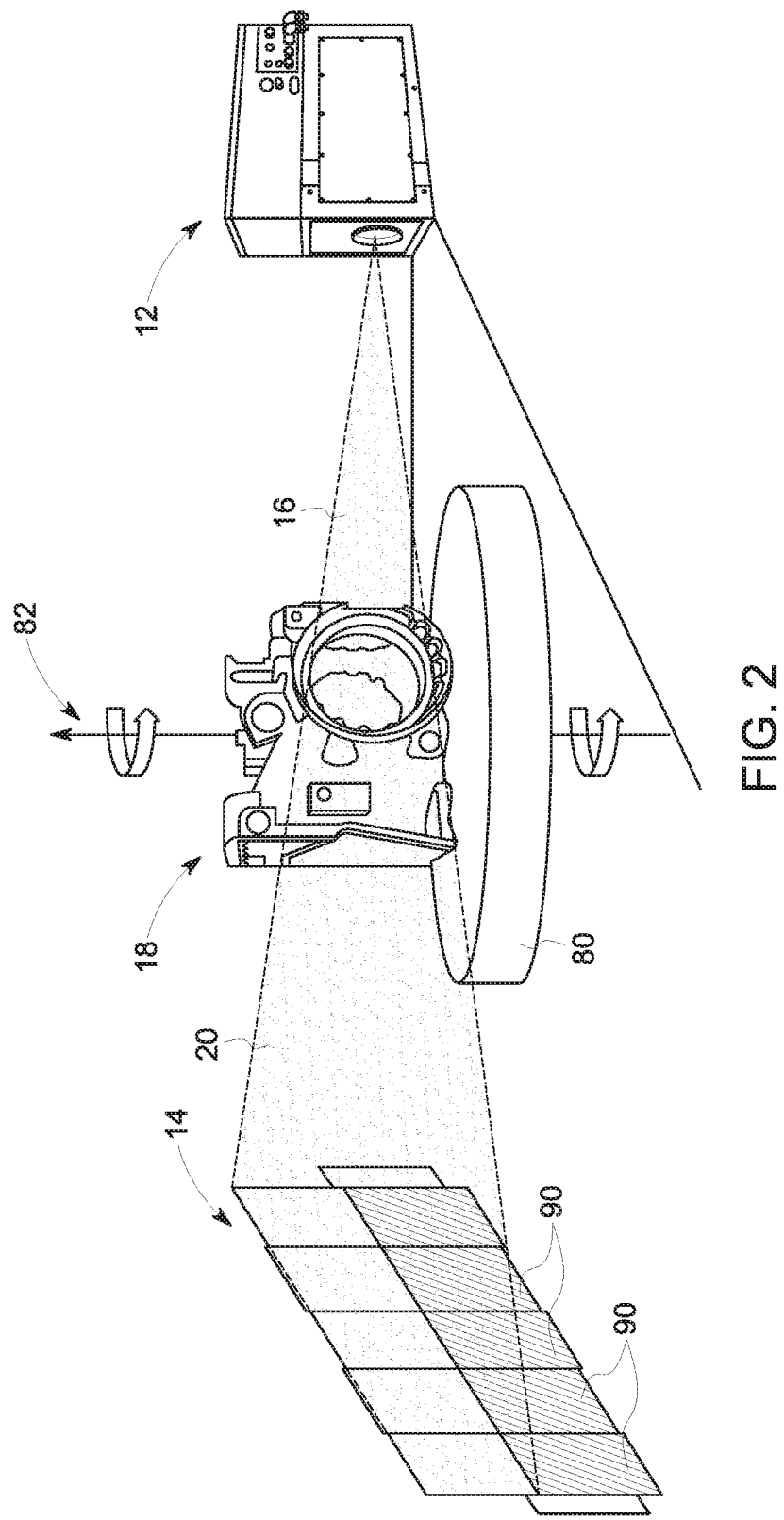
FIG. 2 is a schematic view of an industrial X-ray imaging system using a detector assembly in accordance with aspects of the present disclosure.

Various aspects of the present invention may be further appreciated with respect to FIG. 2, which provides a schematic-type view of certain components of an NDT or NDE system in accordance with the present technique. In this example, an object 18 (e.g., an industrial part or manufactured component) is positioned between an X-ray source 12 and a detector assembly 14. In the depicted example, the object 18 is positioned on a rotating table 80 that rotates about an axis 82 as the object 18 is imaged. During imaging, high-energy X-rays 16 generated by the source 12 are directed toward the object 18 and the detector assembly 14. As discussed herein, the X-rays 16 may be collimated to be a fan-shaped or cone-shaped beam, e.g., a fan-beam or cone-beam, which passes through the object 18, spreading outward as distance from the source 12 increases. A portion of the X-ray radiation 20 passes through or around the object 18 and impacts the detector assembly 14.

As shown in the depicted example, the attenuated X-rays 20 are incident on a detector assembly 14 that is composed of a plurality (i.e., two or more) of abutting detector cassettes 90 that are arranged or positioned so that their respective active areas (i.e., detection areas that generate signals in response to X-rays) are adjacent or overlapping. By way of example, based upon a known region of interest within the object to be images, a suitable field-of-view (FOV) may be determined (e.g., a size and/or shape of the FOV may be determined based on the object, region of interest, and imaging system geometry). Based upon the FOV, a suitable number and arrangement of detector cassettes 90 may be determined that can provide the FOV. The detector cassettes 90 may be mounted or otherwise associated to form a detector assembly 14 providing the FOV for the inspection parameters. In this manner the detector assembly 14 can be customized to have a large and/or custom field-of-view suitable for imaging the object 18, which may itself be large or irregularly shaped.

Figure 3:
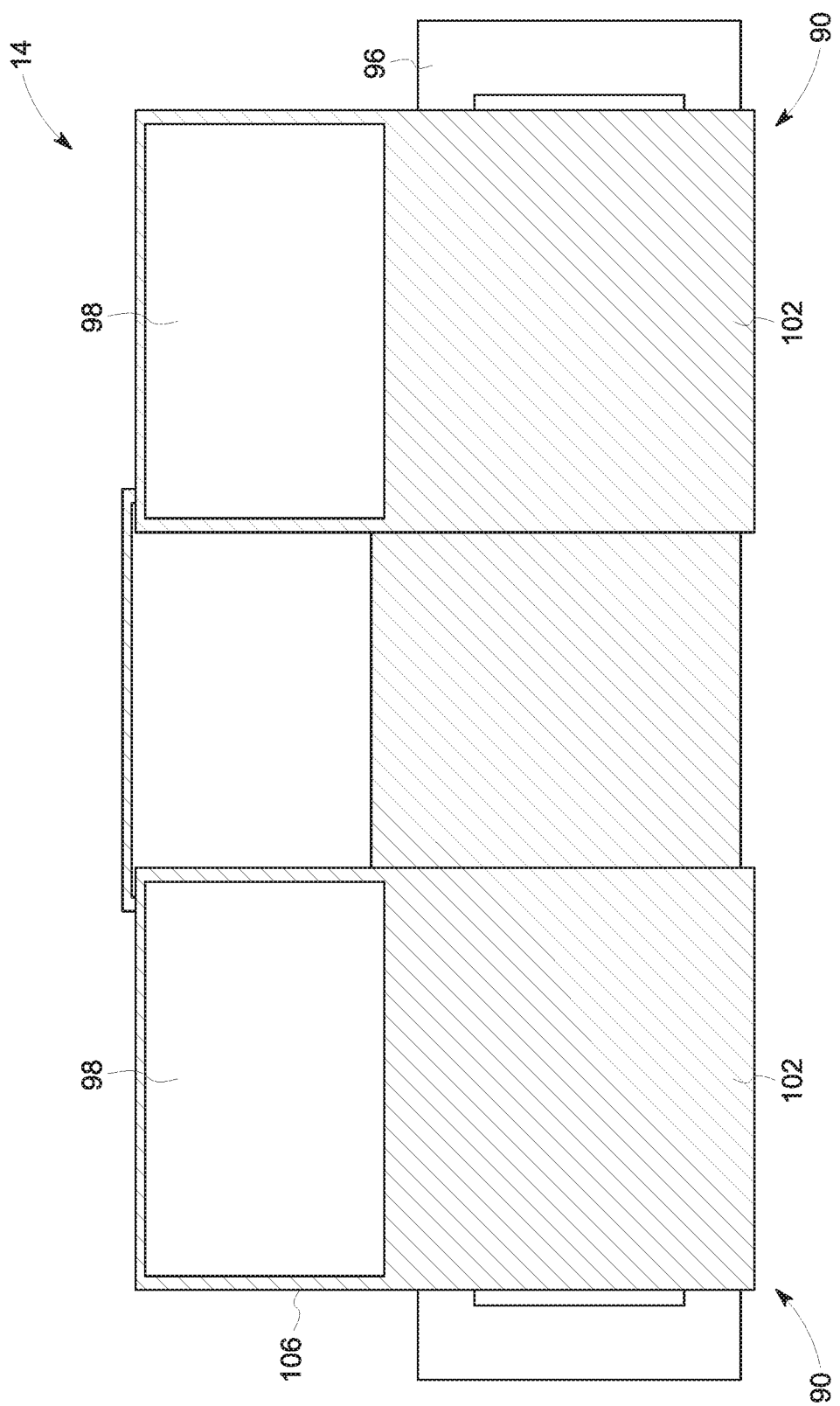
FIG. 3 depicts a front view of the detector assembly of FIG. 2, in accordance with aspects of the present disclosure.
Figure 4:
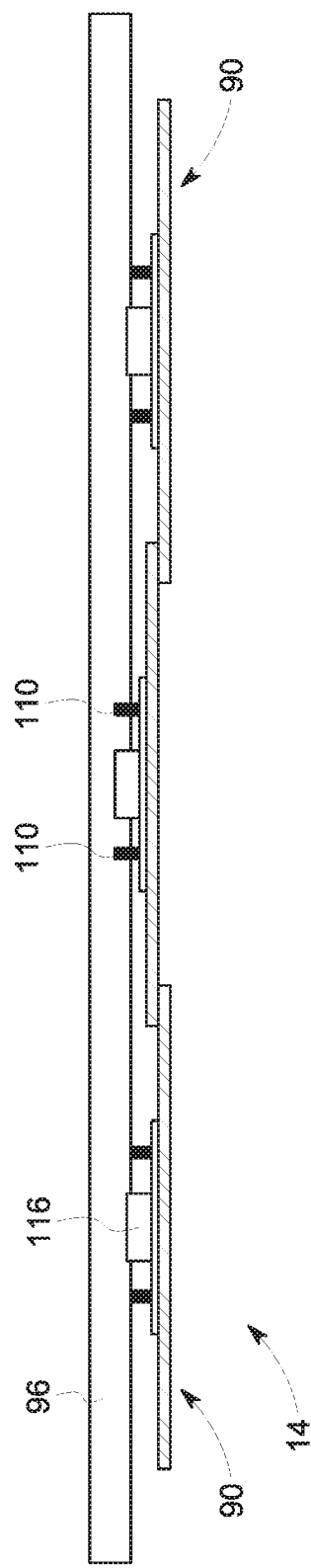
FIG. 4 depicts a top-down view of the detector assembly of FIG. 2, in accordance with aspects of the present disclosure.

Turning to FIGS. 3 and 4, an expanded view of a detector assembly 14 is provided that incorporates aspects of the presently disclosed technique. In this example, a detector assembly 14 consisting of three-overlapping detector cassettes 90 is illustrated. In FIG. 3, a view of the detector assembly 14 from the front (i.e., as seen from the X-ray source 12) is provided while in FIG. 4 the same detector assembly 14 is seen from above (i.e., top-down). In these examples, the detector cassettes 90 are mounted to a support structure (e.g., a detector rail 96) affixed to a wall or other surface. The depicted detector cassettes 90 include an active area 98 configured to be exposed to X-ray radiation and to generate signals in response to such exposure. The depicted detector cassettes 90 also include a non-active area or electronics portion 102 adjacent to the active area 98 in which radiation sensitive electronics (e.g., scan modules, readout electronics and any other electronics (e.g., analog-to-digital (ADC) conversion, filtering, and so forth) susceptible to radiation exposure) are housed. In this manner, these electronic components may be removed from the X-ray beam path during operation so that the active area 98 is exposed to X-rays but the associated electronics are not. By way of example, in one implementation the detector cassette 90 may be 5 cm thick or less (such as 1 cm or 3 cm thick) and have a length of 60 cm and a width of 30 cm. In one such example, the active area 98 may have a length of approximately 30 cm and a width of 15 cm. In another example, the active area 98 may have a length of approximately 40 cm and a width of 20 cm, with a corresponding adjustment to the size of the detector cassette 90. Further, in the depicted example each detector cassette 90 is housed in a separate housing 106 such that the detector cassettes 90 are separate and distinct from one another and can be individually mounted, moved, oriented, and so forth. As noted above, however, in other embodiments multiple detector panels may be housed within a shared or common housing 106 so as to achieve the desired size and form factor, but at the expense of separability.

Turning to FIG. 4, certain additional features may be more easily seen in the top-down view. In particular, with respect to the mounting of the detector cassettes 90, overlap of the detector cassettes 90 (such as between 1 cm to 3 cm of overlap, e.g., 1 cm, 2 cm, or 3 cm of overlap) can be more readily seen. Such overlap can be useful to ensure that there is little or no space in the viewing area that is not covered by an active area 98 of the detector panels, such as due to dead space attributable to housing or the edge of the respective panels. In the detected figure, the detector cassettes 90 forming the detector assembly 14 are mounted to a detector rail 96 (or other support structure). Spacing and/or positioning of the detector cassettes 90 may be mechanically facilitated using on one or more alignment pins 110 that engage with complementary structures on the detector cassette 90 and/or detector rail 96 to ensure placement and spacing of the detector cassettes 90. In the depicted example, the detector cassettes 90 also are connected to thermal ports 116 through which cooling of the electronic components may be accomplished, such as via circulation of air through the housing 106 or other mechanisms for cooling electronic components.

Though the detector cassette examples depicted in FIGS. 3 and 4 are illustrated as flat or planar geometries, in practice the detector cassettes 90 discussed herein may have non-planar geometries. For example, detector cassettes 90 as discussed herein may have non-planar (e.g., curved) geometries such that, when mounted to form a detector assembly 14, the resulting detector assembly 14 has a non-planar detection area. Similarly, though the examples discussed herein are generally shown as having electronics folded flat to one side so as to not be beneath the scintillator (and, correspondingly, away from the X-ray beam path) and to form a planar detector cassette 90, in practice the electronics may be at other angles relative to the active area 98 of the detector cassette while still being outside the beam path when in use. For example, the detector cassette 90 may be formed in an "L" shape such that the electronics protrudes outward at approximately 90° from the active area 98.

Figure 5:
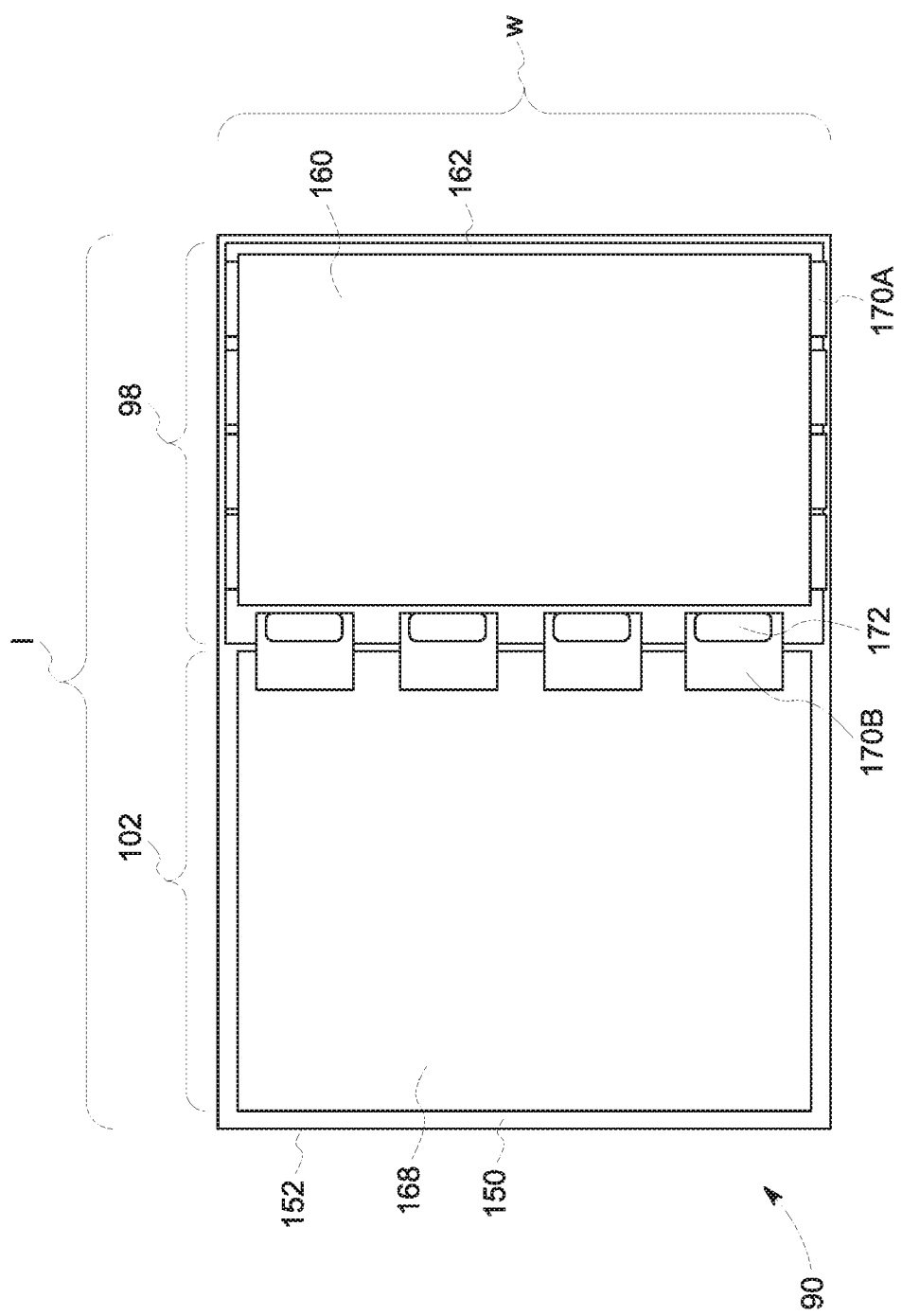
FIG. 5 depicts a plan view of certain of the internal components of a detector cassette, in accordance with aspects of the present disclosure.
Figure 6:
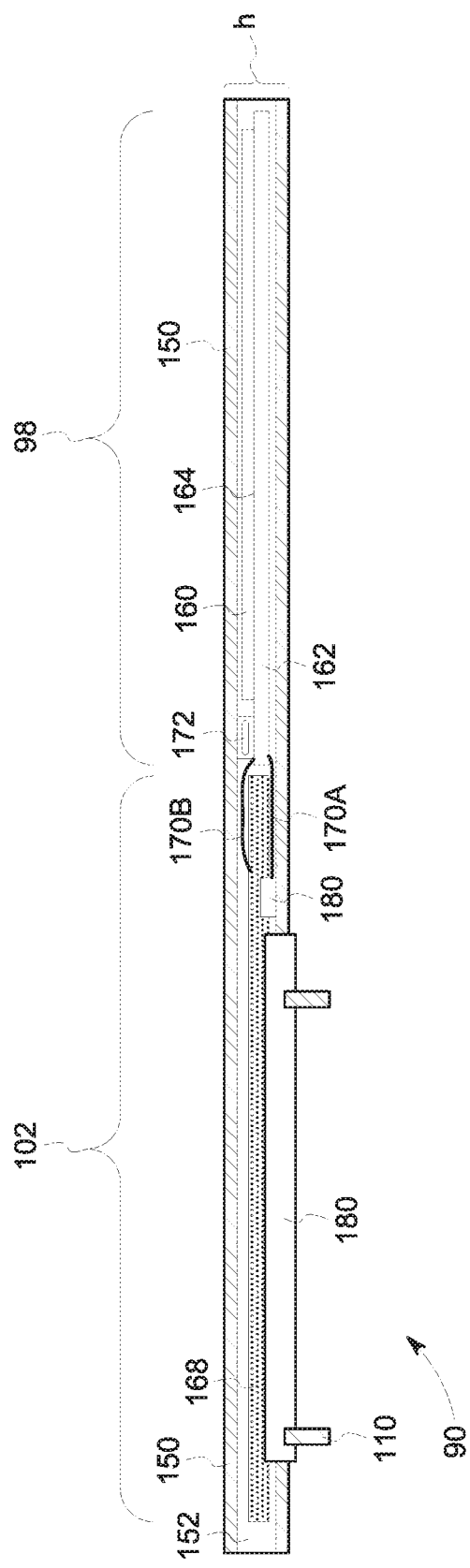
FIG. 6 depicts a side, cut-away view of certain of the internal components of a detector cassette, in accordance with aspects of the present disclosure.

Turning to FIGS. 5 and 6, partial cut-away views of a detector cassette 90 are shown. In FIG. 5, a view of the detector cassette 90 is shown with the cassette cover removed from the topmost layer (though edges of the cassette cover 150 are illustrated on the perimeter) to reveal detector panel components and electronic components of the detector cassette 90. That is, FIG. 5 depicts interior components of the detector cassette 90 as would be seen from the X-ray source 12 with the top layer of the cassette cover 150 removed. In FIG. 6 a cut-away side view of the detector cassette 90 is shown. Both FIGS. 5 and 6 depict a housing that in relevant part include the cassette cover 150 as noted above (e.g., a carbon cover) as well as a cassette frame 152. The cassette cover 150 may be thin and opaque or substantially opaque to optical light and cover the active area 98. In certain implementations, the cassette frame 152, at least in those portions where detector cassettes 90 will or may overlap in forming the detector assembly 14, may be composed of a material having low X-ray absorption and/or scattering properties, such as a plastic composition (e.g., carbon fiber reinforced plastic (CFRP), polycarbonate, PBT, and so forth) or epoxy resins, so as to reduce or minimize artifacts related to stitching data together in the overlap image regions.

As shown in FIG. 5, the detector cassette 90 has an active area 98 that in the depicted example includes a scintillator 160 (e.g., a gadolinium oxysulfide (GOS) or cesium iodide (CsI) scintillator) on a panel substrate 162 (e.g., a glass substrate). The scintillator 160 may be pixelated or non-pixelated and may generate optical or non-X-ray photons in response to exposure to higher energy X-ray photons. The optical or non-X-ray photons may be detected using an array 164 of photodiodes provided beneath the scintillator 160, such as a thin-film-transistor (TFT) array. In practice, the panel components (e.g., the scintillator 160 and associated photodiode array 164) are aligned and mechanically secured with respect to the cassette housing such that the placement of the panel components are known based on knowledge of the housing position. Further one or more interposer structures may be provided between the housing and electronic components to further facilitate securing the panel components to the housing and to ensure a defined spacing and support structure.

The non-active area, i.e., electronics, portion 102 in this example houses any radiation sensitive electronics (e.g., scan modules, field programmable gate arrays (FPGAs), and so forth, which are characterized herein as one or more circuitry boards 168 (e.g., a motherboard). As depicted in the figures and discussed herein, the radiation sensitive electronics are moved away from the path of the X-ray beam (e.g., unfolded and rotated 180° from the active area) to improve radiation hardness and to improve thermal stability, such as to move the FPGAs away from the scintillator 160 and photodiode array 164). Further, in certain embodiments one or more redundant electronics components (e.g., radiation sensitive scan modules) may be provided as part of the electronics assembly so as to improve serviceability and resilience when deployed in a real-world setting.

Such radiation sensitive electronics may be configured to communicate with and read out signals generated at a photodiode array 164 in response to the scintillator 160 being exposed to X-rays. By way of example, the photodiode array 164 (e.g., a TFT array of photodiodes) may be read out as an array of scan line and data lines. In this example, the scan lines may be activated using connected flex circuits 170A positioned along the side of the detector cassette while the data lines may be activated using connected flex circuits 170B positioned along the circuit board 168 and connected to the substrate and data lines via connectors 172. The scan line flex circuit 170A, in one implementation, may be bonded to the panel 162 to connect to the scan lines and routed under the panel 162 to connect to circuit board 168, such as via a zero-insertion force (ZIF) connector 180. As may be appreciated, due to the unfolded configuration in which the readout electronics are separated from the photodiode array 164 (i.e., not underlying the array 164), the connecting conductive traces (such as may be present in the flex circuits 170) may be longer than would be found in a conventional stacked configuration, such as 10 cm to 75 cm in length. Aspects of this configuration are also shown in FIG. 6.

It may further be appreciated that, in certain implementations the panel components (e.g., the scintillator 160, the photodiode array 164, and panel substrate 162) and the electronics components (e.g., circuit board 168) may be constructed so as to be modular (i.e., as separate modules). In such an implementation, a detector cassette 90 may be serviced by replacing either the panel components (i.e., panel module) or the electronic components (electronics module) while leaving the other module in place. For example, a new circuit board 168 may be placed within a detector cassette 90 in place of a board that is not functioning without having to replace the entire detector cassette 90 or the panel components. Conversely, if one or more panel components are not functioning, but the circuit board 168 is functioning, the panel module can be replaced without replacing the circuit board 168.

In the depicted example, and as shown in FIGS. 5 and 6, the detector cassette 90 has a length l, a width w, and a thickness or height h. In one example, the detector cassette 90 can have a length of approximately 30 cm, a width of approximately 15 cm, and a height of approximately 1.5 cm. In addition, as can be seen in FIG. 6, the alignment pins 110 are illustrated to facilitate mounting and/or alignment of the detector cassette 90 to a corresponding mounting surface. An opening 180 is also shown to allow for air cooling and/or a cold plate behind the circuit board 168. In addition, a scatter diffuser structure may be provided as part of the detector cassette 90, such as behind the substrate 162, and may (when present) minimize backscatter that might otherwise generate image artifacts or noise in reconstructed images.

Figure 7:
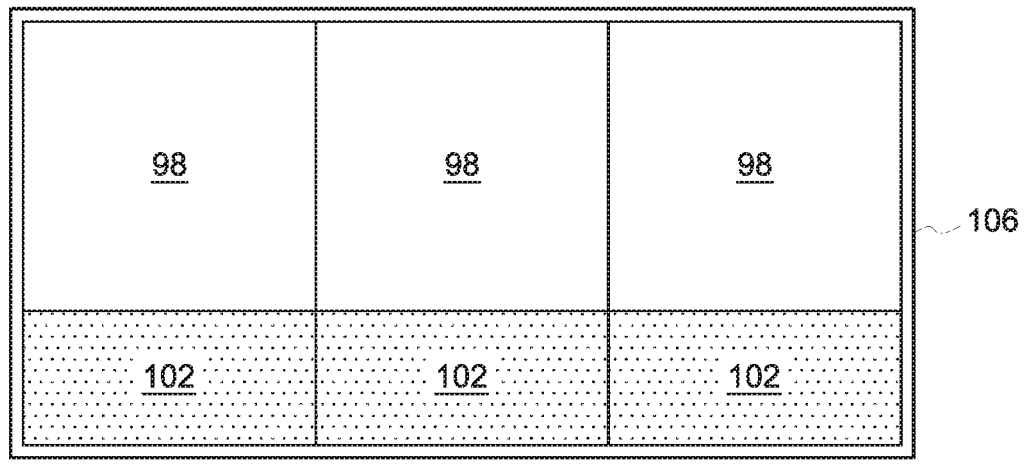
FIG. 7 depicts an embodiment of a plurality of detector cassettes within a single, shared housing, in accordance with aspects of the present disclosure.

While the preceding examples help illustrate one envisioned use case in which discrete detector cassettes 90, each separately housed, are used in combination as a detector assembly 14, in practice other implementations may also be employed. By way of example, and turning to FIG. 7, in one implementation a common or shared housing 106 may contain multiple instances of panel components (e.g., separate scintillators 160 and associated substrates) (indicated in the figure as active area(s) 98) and readout electronics (indicated in the figure as non-active area or electronics portion(s) 102). In this manner, the active areas 98 of each separate panel may be more closely abutted or may be overlapped without having to account for multiple, lateral layers of housing materials that may be present if each were separately housed. In such an embodiment, the housed structure may be construed to be a single detector cassette 90, though multiple instances of panels and electronics may be present within the single cassette housing 106. Further, in such an embodiment a detector assembly 14 may be provided by a single cassette 90 housing multiple panels and circuit boards or by multiple of the combined cassettes 90 abutted next to one another, as more generally described in the preceding examples.

Figure 8:
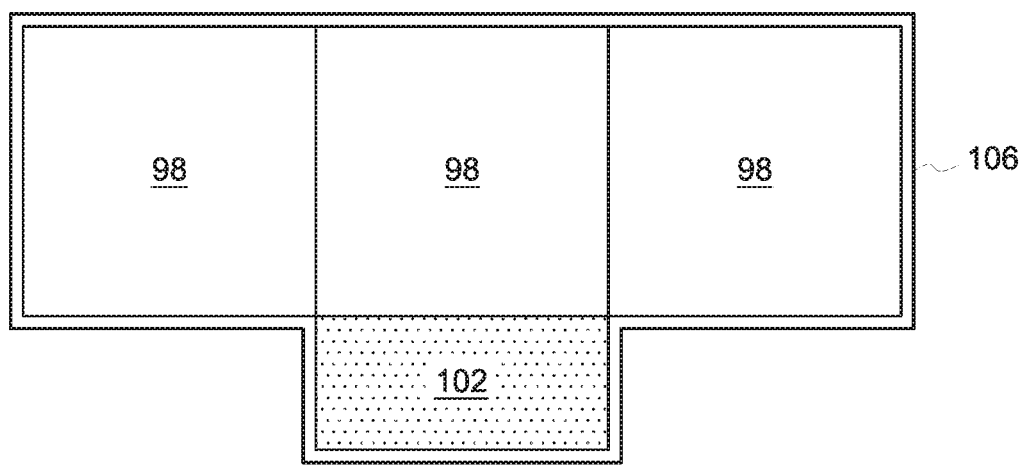
FIG. 8 depicts an embodiment of a plurality of detector panel modules configured work with a single or shared electronics module, in accordance with aspects of the present disclosure.

Turning to FIG. 8, a further implementation is to provide one electronics module (indicated in the figure as non-active area or electronics portion(s) 102) coupled to and supporting multiple panel modules (e.g., scintillators 160 and associated substrates and photodiode arrays 164, indicated in the figures as active area(s) 98). That is, in such an implementation, the electronics that are kept out of the X-ray beam path, here represented as non-active area portion 102, are consolidated onto a single board or module that is connected to multiple panel modules that generate signals in response to X-ray exposure. In the depicted example, this arrangement is shown enclosed within a common or shared housing 106, as with the example shown in FIG. 7.

Figure 9:
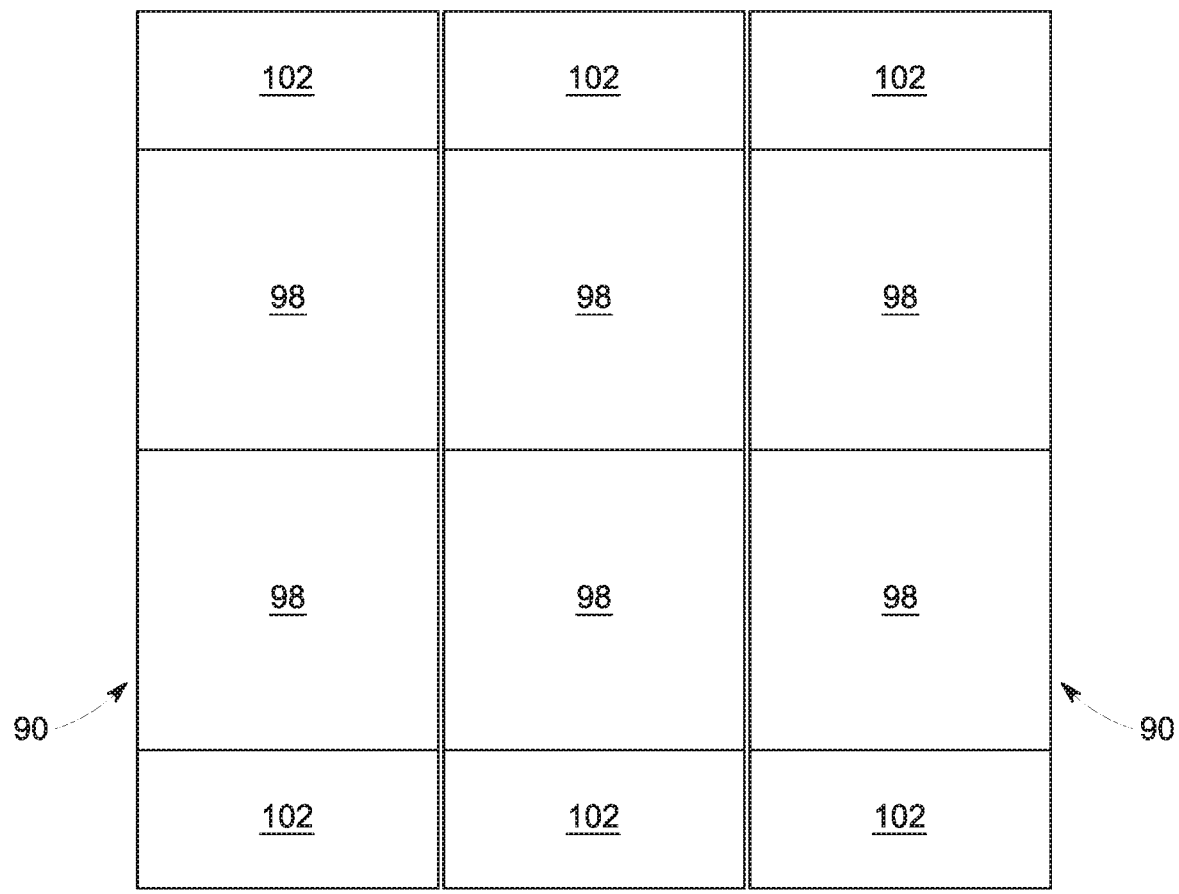
FIG. 9 depicts a three-way buttable arrangement of detector cassettes, in accordance with aspects of the present disclosure.

The preceding examples illustrate lateral (i.e., side-by-side) arrangements of detector cassettes 90 in which each cassette abuts either one other detector cassette 90 (i.e., on one side) or two other detector cassettes 90 (i.e., on two sides). However, in practice a given detector cassette 90 may abut another detector cassette 90 on a third side (i.e., the side opposite the electronic module). That is, in such an embodiment, a given detector cassette 90 may be three-side buttable. Such an arrangement may allow for even greater extents of detector active area and/or greater flexibility in achieving certain active area shapes or extents. By way of example, and turning to FIG. 9, an arrangement of detector cassettes 90, each having a respective active area 98 and non-active area portions 102 are arranged in two rows of three cassettes in each row such that the active areas 98 of all six detector cassettes 90 are effectively combined horizontally and vertically. In this manner, a large FOV can be constructed which may be useful in certain industrial or security screening contexts.

Technical effects of the invention include detector cassettes that may be abutted or overlapped to form a detector assembly suitable for imaging objects that are too large to image using a single detector cassette. Such an assembly of detector cassettes may be assembled to customize a size and/or shape of the field-of-view (FOV) of the detector assembly and may provide image quality consistent with what is obtained using state-of-the-art flat panel detectors. In certain embodiments the radiation-sensitive electronics (e.g., readout electronics) are positioned to the side of the X-ray detecting components (e.g., scintillator, TFT array, and so forth), allowing the cassette to be thin relative to other detector devices (e.g., 5 cm or less in thickness, such as between 1 to 3 cm in thickness) and allowing the electronics to remain outside the X-ray beam path. The electronic components and X-ray detecting components may be provided in a modular format, allowing electronics or panel modules to be replaced without replacing the other module. The detector cassettes may be configured to abut or overlap on two sides (e.g., lateral sides) or three sides (e.g., lateral sides plus one vertical side) so as to minimize or eliminate non-images space between detector cassettes.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An X-ray detector cassette comprising:
   a housing;
   a plurality of panel modules within the housing, each panel module comprising:
      a scintillator; and
      a photodiode array positioned to detect photons emitted by the scintillator, wherein the scintillator and the photodiode array of each panel module is separate from the scintillator and the photodiode array of the other panel modules of the plurality of panel modules; and
   one or more electronics modules within the housing, each electronics module comprising circuitry connected to the photodiode array of at least one panel module, wherein the one or more electronics modules are positioned to the side of the plurality of panel modules so as to remain outside an X-ray beam path during operation;
   wherein the X-ray detector cassette is configured to abut at least one other X-ray detector cassette such that an active area of the X-ray detector cassette abuts respective active areas of the at least one other X-ray detector cassette; and
   wherein at least two panel modules of the plurality of modules are configured to abut each other.

2. The X-ray detector cassette of claim 1, wherein the one or more electronics modules are positioned to the side of the plurality of panel modules so that the X-ray detector cassette is planar.

3. The X-ray detector cassette of claim 1, wherein the X-ray detector cassette has a thickness of less than 5 cm.

4. The X-ray detector cassette of claim 1, wherein the X-ray detector cassette is configured to overlap the at least one other X-ray detector cassette such that the active area of the X-ray detector cassette overlaps respective active areas of the at least one other X-ray detector cassette.

5. The X-ray detector cassette of claim 1, wherein the extent of overlap of the X-ray detector cassette and the at least one other X-ray detector cassette is between 1 cm and 3 cm.

6. The X-ray detector of claim 1, wherein one or more panel modules of the plurality of panel modules are capable of being replaced without replacing respective electronics modules.

7. The X-ray detector of claim 1, wherein the one or more electronics modules are capable of being replaced without replacing respective panel modules.

8. The X-ray detector cassette of claim 1, wherein the one or more electronic modules comprises a single electronic module having its respective circuitry connected to a respective photodiode array of each panel module of the plurality of panel modules.

9. The X-ray detector cassette of claim 1, wherein the plurality of panel modules comprises a first panel module, a second panel module, and a third panel module, and the second panel module abuts both the first panel module and the third panel module.

10. The X-ray detector cassette of claim 1, wherein the X-ray detector cassette is configured to be mounted to a support structure via alignment pins that couple to a portion of the housing that remains outside an X-ray beam path during operation.

11. The X-ray detector cassette of claim 1, wherein the X-ray detector cassette is configured to be coupled to a thermal port when mounted on a support structure to enable cooling of the one or more electronic modules within the housing.

12. An X-ray detector assembly, comprising:
    a plurality of X-ray detector cassettes, each X-ray detector cassette comprising:
       a detector panel module within a housing, wherein the detector panel module comprises a scintillator and a photodiode array positioned to detect photons emitted by the scintillator; and
       an electronics module within the housing, wherein the electronics module comprises circuitry connected to the photodiode array and wherein the electronics module is positioned to the side of the detector panel module so as to remain outside an X-ray beam path during operation;
    a support structure on which the plurality of X-ray detector cassettes are mounted, wherein, when mounted to the support structure, a first subset of X-ray detector cassettes are offset from one another in a first direction corresponding to the direction of the X-ray beam path and overlap in at least a second direction such that the respective detector panel modules of the first subset of X-ray detector cassettes overlap in at least the second direction along a row of X-ray detector cassettes, and wherein a second subset of X-ray detector cassettes are offset from one another in the first direction and overlap in at least a third direction such that the respective detector panel modules of the second subset of X-ray detector cassettes overlap in at least the third direction along a column of X-ray detector cassettes, the third direction being different from both the first direction and the second direction, and the row extends crosswise to the column.

13. The X-ray detector assembly of claim 12, wherein the second direction is substantially perpendicular to the direction of the X-ray beam path.

14. The X-ray detector assembly of claim 12, wherein each X-ray detector cassette has a thickness of less than 5 cm.

15. The X-ray detector assembly of claim 12, wherein the extent of overlap of the X-ray detector cassettes is between 1 cm and 3 cm.

16. The X-ray detector assembly of claim 12, wherein at least one X-ray detector cassette overlaps with other X-ray detector cassettes on three sides.

17. The X-ray detector assembly of claim 12, wherein the third direction is substantially perpendicular to both the direction of the X-ray beam path and the second direction.

18. A method for configuring an X-ray detector assembly, comprising the steps of:
    determining a field-of-view for an object to be inspected;
    determining a number of detector cassettes capable of providing the field-of-view, wherein each detector cassette comprises a detector panel module and an electronics module positioned to the side of the detector panel module so that the electronics module remains outside an X-ray beam path during imaging of the object, and wherein the number is greater than one;

mounting the number of detector cassettes to a support structure to form the X-ray detector assembly providing the field-of-view, wherein a first subset of the detector cassettes, when mounted to the support structure, are offset from one another in a first direction corresponding to a direction of the X-ray beam path and overlap in a second direction such that the respective detector panel modules of the first subset of the detector cassettes overlap in at least the second direction along a row of detector cassettes, and wherein a second subset of the detector cassettes, when mounted to the support structure, are offset from one another in the first direction and overlap in a third direction such that the respective detector panel modules of second subset of the detector cassettes overlap in the third direction, the third direction being different from both the first direction and the second direction along a column of detector cassettes, and the row extends crosswise to the column.

19. The method of claim 18, wherein the second direction is substantially perpendicular to the direction of the X-ray beam path.

20. The method of claim 18, wherein each detector cassette has a thickness of less than 5 cm.

* * * * *